United States Patent [19]
Flicker

[11] 3,975,821
[45] Aug. 24, 1976

[54] INSTRUMENT FOR USE IN ORTHOPEDIC SURGERY

[76] Inventor: Paul L. Flicker, 286 E. Main St., Somerville, N.J. 08876

[22] Filed: Dec. 4, 1975

[21] Appl. No.: 637,909

Related U.S. Application Data
[63] Continuation-in-part of Ser. No. 493,935, Aug. 1, 1974, abandoned.

[52] U.S. Cl. .................................. 30/124; 30/133
[51] Int. Cl.² ........................................ B26B 25/00
[58] Field of Search ............. 30/124, 133, 166, 144, 30/390, 272, 388

[56] References Cited
UNITED STATES PATENTS

| | | | |
|---|---|---|---|
| 2,232,733 | 2/1941 | Scarboro | 30/124 X |
| 2,701,911 | 2/1955 | Maescher | 30/139 X |
| 3,044,171 | 7/1962 | Cecere | 30/166 |
| 3,103,069 | 9/1963 | Gary | 30/124 |
| 3,341,944 | 9/1967 | Ligon | 30/133 |

FOREIGN PATENTS OR APPLICATIONS

| | | | |
|---|---|---|---|
| 930,986 | 9/1947 | France | 30/166 |

Primary Examiner—Al Lawrence Smith
Assistant Examiner—J. C. Peters
Attorney, Agent, or Firm—Sperry and Zoda

[57] ABSTRACT

An apparatus for cutting casts of plaster or other similar materials in the field of immobilization orthopedics including a lightweight and easily grasped hand-piece connected by a hose to a remotely located blower for vacuuming and by a drive shaft to a remotely located driving source, and having a means for cutting casts enclosed in a blower housing for removing any dust created by the cutting, and including a blade sharpener and an auxiliary vacuuming opening for the removal of any localized dust or the like, the blower and drive means being remotely located in a portable unit or a wall unit.

11 Claims, 4 Drawing Figures

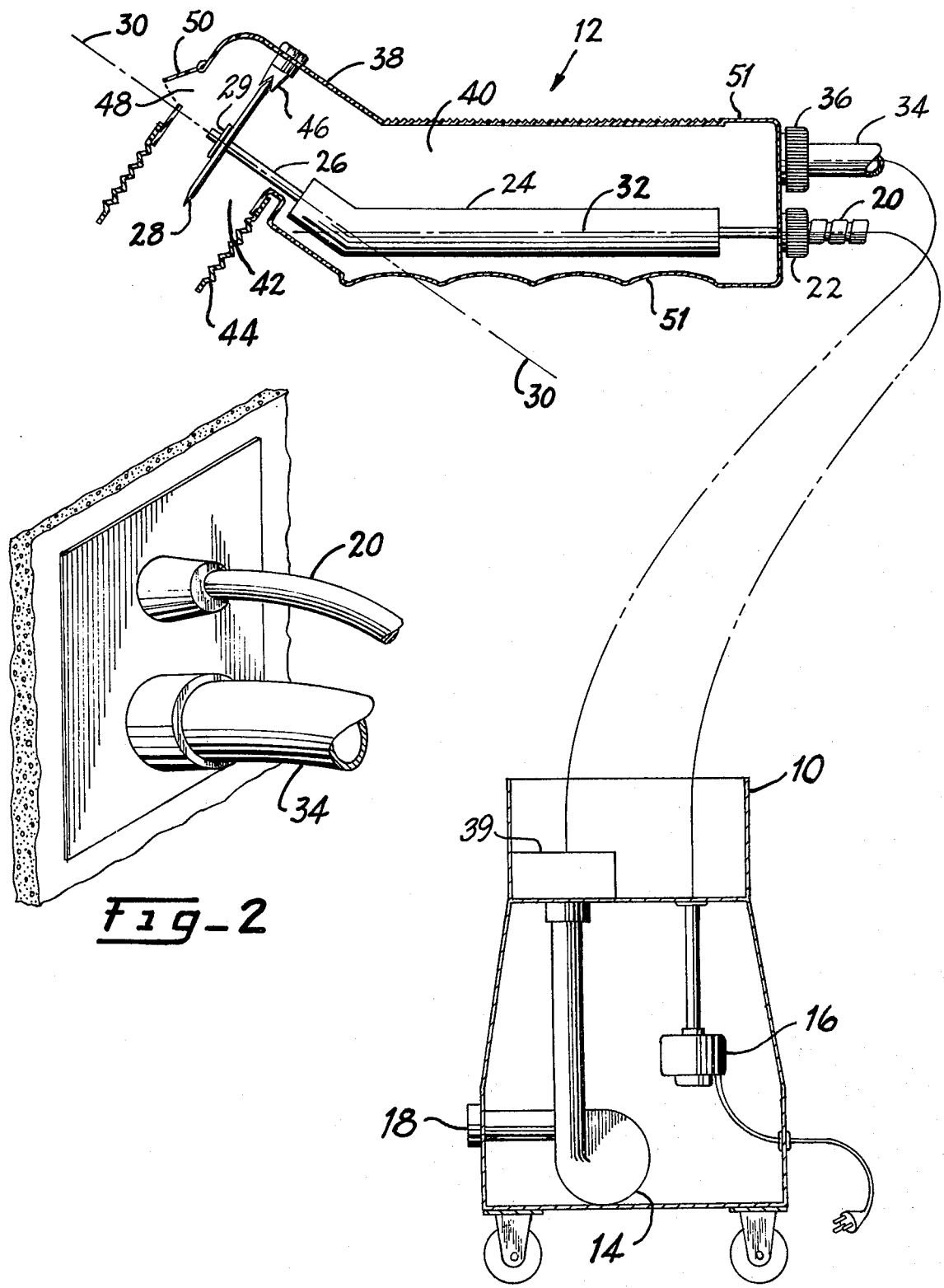

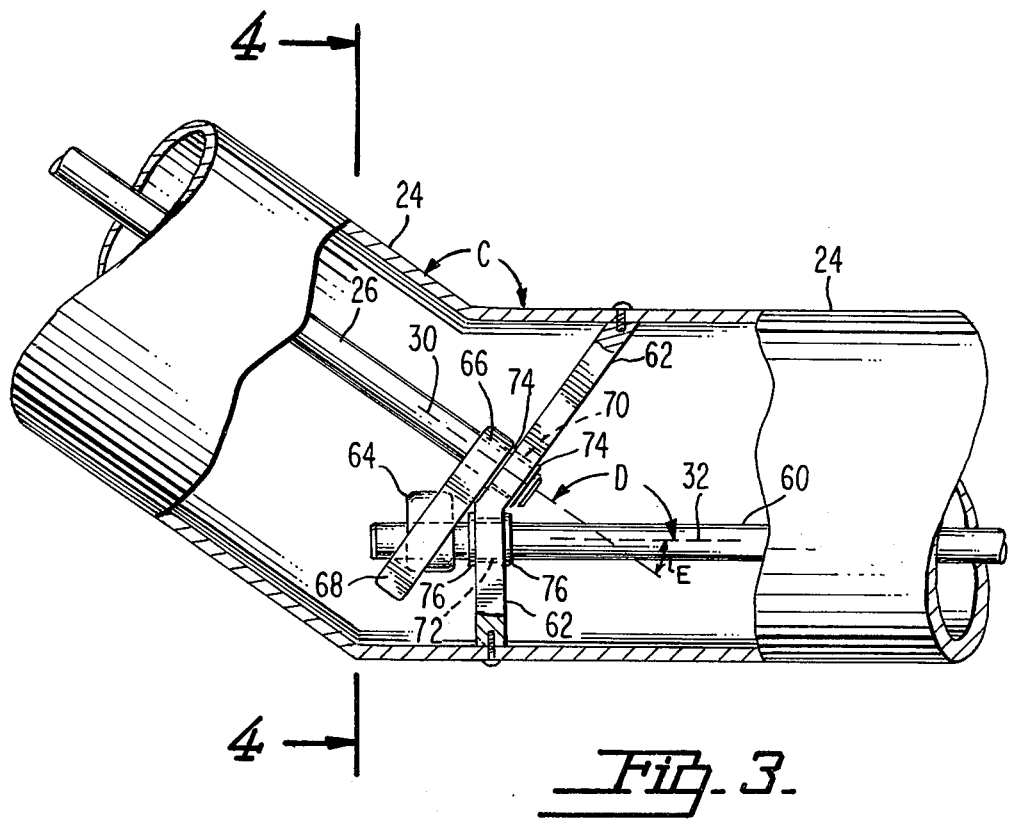
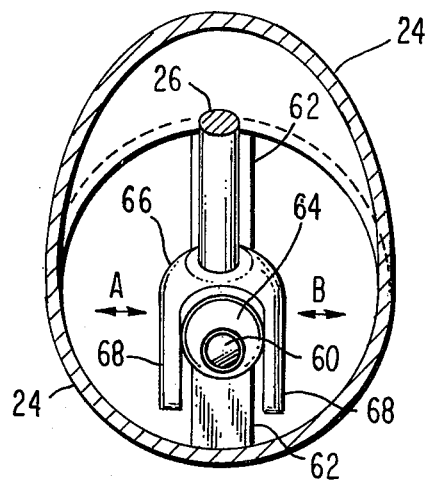

INSTRUMENT FOR USE IN ORTHOPEDIC SURGERY

This invention is a continuation-in-part of U.S. Ser. No. 493,935, filed Aug. 1, 1974, now abandoned.

BACKGROUND OF THE INVENTION

1. Field of the Invention

This invention is in the field of orthopedics, in which reconstruction through immobilization is a common practice. Traumatic and reconstructive orthopedics is a rapidly increasing area of medicine and plaster immobilization offers the most versatility in this area. Plastic materials are sometimes used but they also require removal in a similar fashion.

Cast cutters are often used in hospital areas and doctor's offices where cleanliness and quiet surroundings are desirable. This invention aids in both aspects. Also the suppression of noise is additionally desirable since a loud sawing operation adds greatly to the factor of fear in the patient, especially with younger children.

The use of plaster casts for immobilization is often bypassed by orthopedists and other physicians due to the difficulties and dangers of removal. The advantages of plaster immobilization are often overcome by the inherent difficulties in removal. Plaster casts could be a more attractive remedy if cast removal were an easier and safer operation.

2. Description of the Prior Art

The prior art instruments for cutting casts present many difficulties. Firstly, the motor for driving the blade is located in the hand-piece, which makes it heavy and cumbersome. Since the hand-piece is usually held by one hand of the operator, the additional weight of the motor will induce fatigue if operated for any length of time.

Locating the motor in the hand-piece also increases the noise therefrom in the neighborhood of the patient. This is especially undesirable with smaller children, which is a prominent age group utilizing cast immobilization.

Another problem of the prior art is the generation of heat in the neighborhood of the hand-piece. The friction caused from cutting of the cast by the blade is the primary source of heat but the problem is compounded by the heat generated from the motor when located within the hand-piece. By locating the drive motor remote from the hand-piece and vacuuming in the immediate area of the cutting means the heat generation problem is minimized.

The vacuuming apparatus used in the prior art is inefficient and if cast dust is missed by the main vacuuming opening there is no efficient procedure to clean up the work area without the use of additional apparatus.

The blades used in the prior art tend to become dull quickly since they are cutting through the rather hard cast material currently used. So it would be desirable to have a means for sharpening the blade while located within the hand-piece, and more particularly for automatically sharpening the blade during a cast cutting operation.

The hardness of currently used cast materials requires a large amount of force to be applied to the cutting blade by the operator. Consequently the operator must maintain a very strong grip upon the hand-piece during a cutting operation. The hand-piece of the presently used instruments is coaxial with the axis of oscillation of the cutting blade. This arrangement fails to take into account the 30° backward tilt of a person's hand with respect to his arm when in the strongest grasping position, the powergrip. When the powergrip is made on the presently used hand-piece, the angle of the blade with respect to the arm makes such a grip unusable and an alternate less powerful grasp must be used.

In hospitals there are very often high local concentrations of oxygen in the atmosphere, which can result from overflow or leaks from iron lungs, oxygen tents, oxygen masks and the like. Thus, the danger of fire due to sparking of electric motors is considerable. It is, therefore, desirable to provide a means for shielding the motor drive means from the hospital atmosphere. Such an apparatus would be especially adaptable to modern buildings where wall sockets are often provided in each room for vacuuming and various types of power sources are provided similar to common electrical wall sockets.

The current state of the art in hand-pieces for use in cast cutting is shown by the following patents:

| Patentee | Patent No. |
|---|---|
| Hawley | 1,093,049 |
| Haushalter | 1,542,128 |
| Blair | 2,043,028 |
| Staunt | 2,098,317 |
| May | 3,136,021 |
| Seegers | 3,147,551 |
| Burglaff | 3,173,207 |

These patents relate to various dental tools and other grinding instruments which show arrangements of placing a vacuuming opening in close proximity to a cutting or grinding bit. None of these patents has any application to the field of art of orthopedics or cast cutting. Also, none of these devices places the cutting means coplanar and at an angle with respect to the holding surface to allow for the particular anatomical configuration of the operator. The dental tools show the grinding surface as not coaxial with the hand-gripping surface but this relationship is required by the configuration of the patient's mouth and not by the anatomical requirements of the operator. A dentist is not required to grip his instruments powerfully.

SUMMARY OF THE INVENTION

This invention is an apparatus for cutting casts utilizing a hand-piece with a rapidly oscillating blade. The hand-piece is connected to a remotely located drive source and blower, which are in a portable unit or in a wall unit or partly located in each.

A suction or vacuum hose connects the blower to the vacuum coupling in the hand-piece housing. A flexible drive-shaft connects the drive means to the drive coupling which is located in the housing. The housing encloses the entire hand-piece and forms an enclosure for maintaining an airflow therethrough whenever a vacuuming operation is applied through the vacuum coupling. Therefore, the vacuum coupling is desired to be in fluid flow communication with the enclosure. The enclosure is formed such that the airflow to the blower comes from a primary opening in the housing in the proximate neighborhood of the cutting blade, thereby removing the cast dust produced during cutting operations.

The drive coupling connects the drive shaft to a cam and follower mechanism. This mechanism is located within the hand-piece housing and converts rotational movement of the drive shaft into oscillation of the oscillation shaft and also serves to make the axis of oscillation of the blade coplanar and at an angle with respect to the axis at the drive shaft. This angular inclination is in the range of 30°–35°. The housing will consequently form an oblique angle due to the inclination of the output movement with respect to the input drive. The portion of the housing which is parallel to the axis of the input drive is formed to be readily grasped firmly by the operator of the instrument. Thus, the axis of the cutting blade will be at a coplanar angle with respect to the axis of the forearm of the operator such that it will be convenient for the operator to grip the hand-piece with a powergrip during cutting.

The cutting blade of the apparatus can be chosen to oscillate at a speed and through an angle such that it will cut through the hard cast material but when brought in contact with the padding material under the cast or a person's skin it will merely vibrate the padding or skin without cutting or penetrating.

This invention is preferably made with the cutting blade positioned in abutment with a sharpening device inside the housing to sharpen the blade. The blade may be held in place by a retaining means such as a lock washer or nut device which may be removed to slightly rotate the blade. In this manner the rear portion of the blade will be sharpened during a cutting operation by the front portion of the blade. Another desired option is an auxiliary vacuuming opening for performing minor cleaning jobs in the immediate area of the hand-piece.

The housing is preferably adapted with accordion-like flaps at the vacuuming area adjacent to the blade. These flaps form a flexible extension around the blade and may contact the cast itself during cutting to improve the efficiency of the cleaning and vacuuming of the cast dust.

It is an object of this invention to provide a cast cutting apparatus which is light in weight and easy to use.

It is an object of this invention to provide a cast cutting apparatus which has a housing for the hand-piece that is of a configuration to take into consideration the normal functional position of the wrist and hand and forearm during power activities.

It is an object of this invention to provide a cast cutting apparatus which is maneuverable in almost all positions.

It is an object of this invention to provide a cast cutting apparatus which operates quietly.

It is an object of this invention to provide a cast cutting apparatus which minimizes the heat in the immediate neighborhood of the hand-piece by the removal of heat associated with the motor and by the vacuuming of heated air in the immediate neighborhood of the heat generated by the friction between the cast and the blade.

It is an object of this invention to provide a cast cutting apparatus which includes a sharpening device.

It is an object of this invention to provide a cast cutting apparatus which efficiently removes plaster dust.

It is an object of this invention to provide a cast cutting apparatus which includes an auxiliary vacuuming opening for removing any localized debris in the immediate area of the hand-piece.

It is an object of this invention to provide a cast cutting apparatus which is portable without comprising efficiency of cutting or vacuuming.

It is an object of this invention to provide a cast cutting apparatus which is safer than prior apparatus.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a schematic representation of one embodiment of the present invention;

FIG. 2 is a schematic representation of an alternate embodiment using wall sources;

FIG. 3 is one of many possible embodiments of the cam and follower mechanism of FIG. 1; and FIG. 4 is a crossectional view of FIG. 3 along lines 4—4.

DETAILED DESCRIPTION OF THE PREFERRED EMBODIMENT

In FIG. 1 a schematic diagram of an embodiment of the present invention is illustrated in combination with a portable blower and drive source unit 10 located remotely from the hand-piece, generally denoted 12. Unit 10 is shown with a blower 14 and a drive means 16. Blower motor 14 has an outlet 18 for exhaust or waste.

Drive motor 16 is shown connected to flexible drive shaft 20 which is attached to drive coupling 22. Drive shaft 20 is of sufficient length to allow the unit 10 to be located remotely from hand-piece 12. Cam and follower mechanism 24 is located within housing 12 and is connected with drive shaft 20 at drive coupling 22. Cam and follower mechanism 24 is shown here with a rod or oscillation shaft 26 extending therefrom. Circular cutting blade 28 is attached to the end of shaft 26 such that the plane of the blade is perpendicular to the rod axis 30. The axis of the drive output of mechanism 24 is the same axis as axis 30 of shaft 26.

The axis of the input drive coupling 22 is shown as axis 32 in FIG. 1. The mechanism 24 is constructed such that the output axis 30 is coplanar and at an angle with respect to the axis 32 at an inclination of approximately 30°–35°. Mechanism 24 is secured to the interior walls of hand-piece 12 by any convenient bracketing assembly (not shown). This is an important anatomical consideration as will be discussed more fully below.

The blower 14 located in portable unit 10 is shown in FIG. 1 connected to vacuuming or suction hose 34 to pull air therefrom which is then expelled through outlet 18. The vacuuming hose 34 is chosen long enough to allow portable unit 10 to be located remotely from hand-piece 12. The other end of hose 34 is attached to vacuuming coupling 36, located in housing 38. As an additional feature, vacuum hose 34 can have located therein a filtering means 39 to eliminate the passage of cast dust into the blower 14 which could cause clogging and to eliminate the expulsion of cast dust into the atmosphere through outlet 18.

Housing 38 forms an interior enclosure 40 which is hermetically sealed except for vacuuming coupling 36 and primary vacuuming opening 42. The drive coupling 22 acts as an air seal between enclosure 40 and the ambient environment. Consequently, when blower 14 is operated, air is pulled into enclosure 40 through primary opening 42.

Primary opening 42 is located around cutting blade 28 such that dust produced from cast cutting will pass through the vacuuming system. To improve the efficiency of the vacuuming operation a baffle extension 44 is provided about primary vacuuming opening 42. Extension 44 is an accordion-like extension of the primary vacuuming opening which can abut the cast during cutting and thereby greatly reduce the likelihood of any cast dust escaping the vacuuming system. Extension 44 can be of any material and is detachable from housing 38 so as to be easily replaceable. Extension 44 is preferably formed of a translucent material to facilitate the operator's view of the cutting operation.

Due to the hard plaster or plastic materials of which casts are presently being made, it is frequently necessary to replace the cutting blade. To eliminate this additional expense and maintenance, this invention is equipped with a sharpening means 46 located with housing 38. To assure use of a sharpened blade section, the retaining means 29 can be removable. Retaining means 29 secures cutting means 28 fixedly on shaft 26 and is releasable to allow manual rotation of blade 28 such that the sharpened portion of blade 28 will be exposed and the dull, most recently used, section will be sharpened during the oscillating movement by abutting cutting means 46.

Despite all precautions to increase the efficiency of the vacuuming system, some cast dust will invariably escape. To facilitate the removal of this escaped cast dust or removal of any other localized debris, the cast cutter is provided with a secondary vacuuming opening 48. Preferably, opening 48 is adapted with an easily flippable valve 50 for opening and closing the secondary opening 48.

The external shape of housing 38 is largely dictated by the inclination of shaft 26 at the output of mechanism 24 with respect to the input of mechanism 24 at drive coupling 22. This inclination is desirable to take into consideration the 30°–35° angle of a person's wrist with respect to his forearm when his hand is in the most powerful grip. The section 51 of the housing 38 which is gripped is shown in FIG. 1 surrounding mechanism 24. Thus, the axis of oscillation of blade 28 will be inclined at an angle with respect to the operator's wrist to compensate for the angle of inclination between the operator's wrist and his forearm and thereby facilitate the use of the power grip which is required in an activity as strenuous as cast removal. The combination of the inclination of the blade and the use of a lightweight hand-piece greatly decreases the fatigue factor of all the prior art instruments.

FIG. 2 illustrates another preferred embodiment of the present invention whereby the blower and the drive source are in a remotely located wall unit, such that the noise and heat associated with these sources is removed from the immediate vicinity of the cutting operation. Of course, it must be appreciated that some hospitals might have wall connections for only vacuum or for only power in which case the other source could be located remotely in the portable unit.

The internal gearing of gear mechanism 24 can be chosen from any system which converts rotational input into oscillation output with an inclination therebetween of 30° to 35°. One such mechanism is shown in FIGS. 3 and 4 in which axis 30 and 32 are shown at 35° with respect to one another. Rotating input 60 passes through retaining bracket 62 to receive a circular offset cam 64 thereon. Bracket 62 also includes mounted therein the bottom end of oscillating blade shaft 26. Fixedly positioned on shaft 26 is a fork 66 have cam followers 68 extending downward therefrom around cam 64. Shaft 26 is mounted for rotary oscillation in bracket 62 inside of bearing 70 similarly to shaft 60 being mounted within bearing 72. Shafts 26 and 60 are preventing from sliding axially within bearings 70 and 72 by retaining ring sets 74 and 76 respectively.

During operation as shaft 60 rotates the offset cam 64 will similarly rotate. Cam 64 will cause followers 68 to reciprocate as shown by arrows A and B in FIG. 4 such that the fixed connection of shaft 26 within fork 66 will cause rotary oscillation of shaft 26 and consequently blade 28. It should be noted that the inclination achieved by this gearing is 30°–35°. Angle E is shown as 35°. Also shown are angles C and D of 145° which are complementary with angle E in that the sum of angles E and D or angles E and C is 180° or a straight line. Many other similar cam and follower systems could be used within mechanism 24.

While two particular embodiments of this invention have been shown in the drawings and described above, it will be apparent, that many changes may be made in the form, arrangement and positioning of the various elements of the combination. In consideration thereof, it should be understood that preferred embodiments of this invention disclosed herein are intended to be illustrative only and not intended to limit the scope of the invention.

I claim:

1. Apparatus for cutting casts of plaster or other similar materials in the field immobilization orthopedics comprising;
   a. a flexible drive shaft connected to a remotely located drive means for rotation of said drive shaft;
   b. a flexible vacuum hose connected to a remotely located blower;
   c. a hand-piece, said hand-piece further comprising;
      1. a housing defining an enclosure, said housing including an exterior housing surface thereof having a generally cylindrical configuration to facilitate being firmly gripped by a hand of the operator;
      2. a vacuum coupling in said housing having fluid flow communication with the interior of said enclosure, said vacuum hose being connected to said vacuum coupling;
      3. a drive coupling in said housing, said drive shaft being attached to said drive coupling and extending within said housing;
      4. a cutting means located at least partially in said housing to form a primary vacuum in the neighborhood of said cutting means;
      5. an oscillation shaft secured to said cutting means at an angle with respect to said drive shaft in said housing; and
      6. a cam and follower mechanism located within said housing and being secured to said oscillation shaft and said drive shaft to cause said oscillation shaft to oscillate upon rotation of said drive shaft, said mechanism maintaining said oscillation shaft and said drive shaft in a position at an angle with respect to one another and coplanar with respect to one another such that the axes of said oscillation shaft and said drive shaft are positioned in an intersecting orientation.

2. The apparatus as defined in claim 1 wherein said cutting means is in a fixed angular orientation with respect to said exterior housing surface.

3. The apparatus as defined in claim 1 wherein said cutting means further comprises a blade connected to said oscillation shaft.

4. The apparatus as defined in claim 3 wherein said blade is circular.

5. The apparatus as defined in claim 3 wherein the axis of oscillation of said blade is approximately at an angle of 30°–35° with respect to the axis of said drive shaft.

6. The apparatus as defined in claim 1 wherein a section of said housing is of a generally cylindrical configuration to be able to be grasped by the hand of a person, said section being parallel to the axis of said drive shaft.

7. The apparatus as defined in claim 1 wherein said hand-piece includes a sharpening means for sharpening said cutting means.

8. The apparatus as defined in claim 1 wherein said housing defines a secondary vacuum opening for auxiliary vacuuming operations.

9. The apparatus as defined in claim 8 including a valve means for selectively opening and closing said secondary vacuum opening.

10. The apparatus as defined in claim 1 wherein said housing includes a detachable flexible extension around said primary vacuum opening which abuts a cast during cutting to facilitate removal of cast dust in the neighborhood of said cutting means.

11. The apparatus as defined in claim 1 further comprising a filtering means located between said vacuum coupling and said blower.

* * * * *